United States Patent [19]

Grollier et al.

[11] Patent Number: 4,867,966
[45] Date of Patent: Sep. 19, 1989

[54] COSMETIC COMPOSITIONS BASED ON CATIONIC POLYMERS AND ALKYLOXAZOLINE POLYMERS

[75] Inventors: Jean F. Grollier, Paris; Claude Dubief, Le Chesnay, both of France

[73] Assignee: L'Oreal, Paris, France

[21] Appl. No.: 97,703

[22] Filed: Sep. 17, 1987

[30] Foreign Application Priority Data

Sep. 19, 1986 [LU] Luxembourg ............................ 86599

[51] Int. Cl.$^4$ ............................................. A61K 7/11
[52] U.S. Cl. ........................................ 424/71; 424/47; 424/78
[58] Field of Search .................... 424/47, 70, 71, 78, 424/DIG. 1, DIG. 2

[56] References Cited

U.S. PATENT DOCUMENTS

| 3,579,630 | 5/1971 | Herz et al. ............................ 424/47 |
| 3,910,862 | 10/1975 | Barabas et al. ................... 424/71 X |
| 3,917,817 | 11/1975 | Vanlerberghe et al. ............. 424/70 |
| 3,980,091 | 9/1976 | Dasher et al. ........................ 132/7 |
| 4,013,787 | 3/1977 | Vanlerberghe et al. ............. 424/70 |
| 4,165,367 | 8/1979 | Chakrabarti ..................... 424/71 X |
| 4,172,887 | 10/1979 | Vanlerberghe et al. ............. 424/70 |
| 4,189,468 | 2/1980 | Vanlerberghe et al. ............. 424/70 |
| 4,277,581 | 7/1981 | Vanlerberghe et al. ....... 525/419 X |
| 4,521,404 | 6/1985 | Lorenz et al. ...................... 424/71 |

FOREIGN PATENT DOCUMENTS

| 0095238 | 11/1983 | European Pat. Off. . |
| 0122324 | 10/1984 | European Pat. Off. . |
| 1310140 | 3/1973 | United Kingdom . |
| 2136689 | 9/1984 | United Kingdom . |

Primary Examiner—Ellis P. Robinson
Assistant Examiner—Susan S. Rucker
Attorney, Agent, or Firm—Fleit, Jacobson, Cohn, Price, Holman & Stern

[57] ABSTRACT

Cosmetic composition intended for hair treatment and care, characterized in that it contains, in a cosmetically acceptable medium, at least one alkyloxazoline polymer of formula:

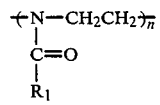

in which $R_1$ is a $C_1$-$C_4$ alkyl radical, and at least one cationic polymer.

13 Claims, No Drawings

COSMETIC COMPOSITIONS BASED ON CATIONIC POLYMERS AND ALKYLOXAZOLINE POLYMERS

The present invention relates to new cosmetic compositions intended in particular for hair treatment and care, containing a polymer derived from alkyloxazoline and a cationic polymer.

Different polymers have been used, for many years, in compositions intended for hair treatment and care, with a view to modifying the properties of the latter, especially with regard to appearance, shape-retention, shape, ease of combing, touch, softness and sheen and the like.

Anionic polymers or nonionic polymers or amphoteric polymers, or alternatively, a combination of cationic and anionic polymers or of amphoteric polymers with anionic or cationic polymers are employed for this purpose.

In the state of the art, some nonionic polymers such as vinylpyrrolidone/vinyl acetate polymer or polyvinylpyrrolidone have also been combined with cationic polymers.

Polymers derived from oxazolines are known in themselves and French Pat. No. 1,553,988 describes in particular the application of some of these polymers in hair-dressing compositions which are applied more particularly by spraying.

It should be noted that although polymers derived from alkyloxazoline contribute slight waviness to the hair style, they are not sufficiently effective with regard to sheen, shape-retention, softness and disentangling.

The Applicant Company has surprisingly discovered that when alkyloxazoline polymers were combined with cationic polymers, they led to a remarkable effectiveness on hair, especially with regard to properties of disentangling, softness, sheen, liveliness, buoffancy, shape, touch and appearance.

The subject of the invention is therefore a cosmetic composition mainly intended for hair treatment and care, containing at least one alkyloxazoline polymer and at least one cationic polymer.

Another subject of the invention consists of a treatment method, in particular for hair, which consists in applying to them at least one alkyloxazoline polymer and at least one cationic polymer.

Other subjects of the invention will become apparent on reading the description and examples which follow.

The cosmetic composition according to the invention is essentially characterized in that it contains at least one oxazoline polymer of formula:

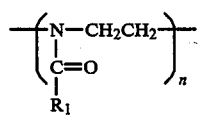
(I)

in which $R_1$ is a $C_1$–$C_4$ lower alkyl radical and preferably an ethyl group, n has a value such as the polymer has a molecular weight of at least 10,000, and at least one cationic polymer in a cosmetically acceptable medium.

The oxazoline polymers of formula (I) have a molecular weight greater than 10,000, generally between 20,000 and 1 million and preferably between 50,000 and 500,000 and are prepared by the polymerization of 2-alkyl-2-oxazoline. The preferred polymers are ethyloxazoline homopolymers with a molecular weight between 20,000 and 1 million and more particularly those sold under the name Polymer XAS-10874 by DOW CHEMICAL which have molecular weights from 50,000 to 500,000.

The cationic polymers are more particularly chosen from amongst polymers which contain primary, secondary, tertiary and/or quaternary amine groups, which form part of the polymer chain or are linked thereto and which have a molecular weight between 500 and approximately 5,000,000 and preferably between 1,000 and 3,000,000.

Among these polymers, there may be mentioned, more particularly, quaternized proteins, quaternized polysiloxanes and polymers of the quaternary polyammonium, polyaminoamide or polyamine type.

A. The quaternized proteins are in particular polypeptides which are modified chemically and which carry, at the end of the chain or grafted thereto, quaternary ammonium groups. Among these proteins, there may be mentioned, in particular:

collagen hydrolysates carrying triethylammonium groups, such as products sold under the name "QUAT-PRO E" by MAYBROOK and referred to in the CTFA dictionary as "triethonium hydrolyzed collagen ethosulfate";

collagen hydrolysates carrying trimethylammonium or dimethylstearylammonium chloride groups, sold under the name "QUAT-PRO S" by MAYBROOK and referred to in the CTFA dictionary as "steartrimonium hydrolyzed collagen";

hydrolysates of animal proteins, carrying dimethylbenzylammonium groups, such as products sold under the name "CROTEIN BTA" by CRODA and referred to in the CTFA dictionary as "benzyltrimonium hydrolyzed animal protein";

protein hydrolysates carrying on the polypeptide chain quaternary ammonium groups containing at least one alkyl radical containing 1 to 18 carbon atoms.

Among these protein hydrolysates, there may be mentioned, inter alia:

CROQUAT L, the polypeptide chain of which has an average molecular weight of approximately 2,500 and the quaternary ammonium group of which contains a $C_{12}$ alkyl group;

CROQUAT M, the polypeptide chain of which has an average molecular weight of approximately 2,500 and the quaternary ammonium group of which contains a $C_{10}$–$C_{18}$ alkyl group;

CROQUAT S, the polypeptide chain of which has an average molecular weight of approximately 2,700 and the quaternary ammonium group of which contains a $C_{18}$ alkyl group; and CROTEIN Q, the polypeptide chain of which has an average molecular weight of the order of 12,000 and the quaternary ammonium group of which contains at least one alkyl group containing 1 to 18 carbon atoms.

These different products are sold by CRODA.

Other quaternized proteins are those which correspond to the formula:

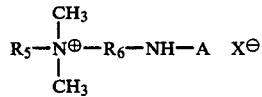
(II)

in which A denotes a protein residue derived from collagen protein hydrolysates, $R_5$ denotes a lipophilic group containing up to 30 carbon atoms, $R_6$ represents an alkylene group containing 1 to 6 carbon atoms and $X^\ominus$ represents an anion derived from an organic or inorganic acid; these proteins have a molecular weight between 1,500 and 10,000, preferably between 2,000 and 5,000. The preferred products are those sold under the name "LEXEIN QX 3000" by INOLEX, which is referred to in the CTFA dic-tionary as "cocotrimonium collagen hydrolysate".

B. Another family of cationic polymers consists of silicone cationic polymers. Among these polymers, there may be mentioned:

(a) quaternized polysiloxanes, referred to in the CTFA dictionary as "amodimethicone" and corresponding to the formula:

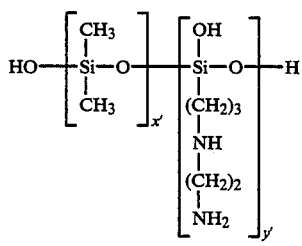
(III)

in which x' and y' are integers which depend on the molecular weight which is generally between 5,000 and 10,000;

(b) silicone cationic polymers corresponding to the formula:

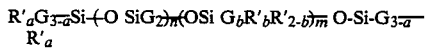
(IV)

in which:

G is a hydrogen atom, or phenyl group, OH, a $C_1$-$C_8$ alkyl group and preferably a methyl group, a denotes 0 or an integer from 1 to 3 and preferably 0, b denotes 0 or 1 and preferably 1, the sum (n+m) is an integer from 1 to 2,000 and preferably from 50 to 150, it being possible for n to denote a number from 0 to 1,999 and preferably from 49 to 149 and it being possible for m to denote an integer from 1 to 2,000 and preferably from 1 to 10, R' is a monovalent radical of formula $C_qH_{2q}L$ in which q is a number from 2 to 8 and L is chosen from amongst the following groups:

—N(R'')—CH$_2$—CH$_2$—N(R'')$_2$

—N(R'')$_2$

—N$^\oplus$(R'')$_3$A$^\ominus$

—N$^\oplus$(R'')H$_2$A$^\ominus$

—N(R'')CH$_2$—CH$_2$—N$^\ominus$(R'')H$_2$A$^\ominus$, in which R'' may denote hydrogen, phenyl, benzyl or a monovalent saturated hydrocarbon radical and preferably an alkyl radical containing 1 to 20 carbon atoms and A$^\ominus$ represents a halide ion such as chloride, bromide, iodide or fluoride.

A particularly valuable product which falls within this definition is the polymer called "trimethylsilylamodimethicone" corresponding to the formula:

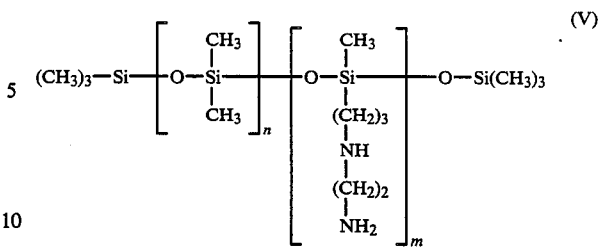
(V)

in which n and m have the meanings given above (formula IV). Such polymers are described in the Patent Application EP-A-95,238; and (c) silicone cationic polymers corresponding to the formula:

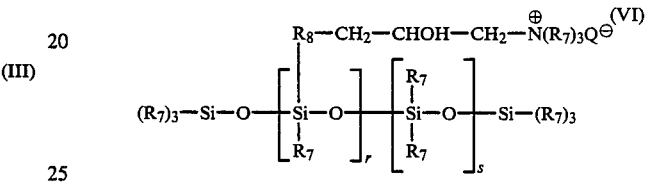
(VI)

in which:

$R_7$ denotes a monovalent hydrocarbon radical containing 1 to 18 carbon atoms and in particular an alkyl or alkenyl radical and preferably a methyl radical;

$R_8$ denotes a divalent hydrocarbon radical, preferably a $C_1$-$C_{18}$ alkylene radical or a $C_1$-$C_{18}$, and preferably $C_1$-$C_8$, divalent alkylenoxy radical;

$Q^\ominus$ is a halide ion, preferably chloride;

r represents a statistical mean value from 2 to 20 and preferably from 2 to 8 and s represents a statistical mean value from 20 to 200 and preferably from 20 to 50.

Such polymers are described more particularly in the Patent US-A-4,185,087.

A particularly preferred polymeer forming part of this class is the polymer sold by UNION CARBIDE under the name "UCAR SILICONE ALE 56" which is characterized by a flashpoint of 60° C. according to the standard ASTDM-93, a viscosity of 0.011 Pa.s at an active substance concentration of 35% and at 25° C. and by a total base number of 0.24 meq/g.

When these silicone polymers are employed, a particularly beneficial manner of application is their use together with nonionic surfactants and optionally with cationic surfactants. For example, it is possible to use in the compositions according to the invention, the commercial product sold under the name "EMULSION CATIONIQUE DC 929" (cationic emulsion DC 929) by DOW CORNING which contains amodimethicone of formula (III), a cationic surfactant corresponding to the formula:

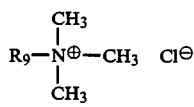
(VII)

in which $R_9$ denotes a mixture of alkenyl and/or alkyl radicals containing 14 to 22 carbon atoms, derived from tallow fatty acids, and a nonionic surfactant of formula:

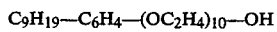

which is known under the name "NONOXYNOL 10".

Another composition which can be employed in this embodiment of the invention is the composition containing the product sold under the name "DOW CORNING Q2 7224" by DOW CORNING which contains, in the combined form, trimethylsilylamodimethicone of formula (V), a nonionic surfactant of formula:

$C_8H_{17}-C_6H_4-(OCH_2CH_2)_nOH$ where n=40 which is also called octoxynol-40, a nonionic surfactant of formula:

$C_{12}H_{25}-(OCH_2-CH_2)_nOH$ where n=6 which is also called isolaureth-6, and glycol.

C. The quaternary polyammonium, polyaminoamide or polyamine type of polymers which can be employed according to the present invention are described in particular in French Pat. Nos. 8,207,996 or No. 8,404,475 of the Applicant Company.

Among these polymers, there may be mentioned:

(1) vinylpyrrolidone/dialkylaminoalkyl acrylate or methacrylate copolymers, which may be quaternized or otherwise, such as the products sold under the name "GAFQUAT" by GAF CORPORATION, such as, for example, "GAFQUAT 734 or 755" or the products called "COPOLYMER 845, 958 and 937". These polymers are described in detail in French Pat. Nos. 2,077,143 and 2,393,573.

Vinylcaprolactam/vinylpyrrolidone/dialkylaminoalkyl methacrylate or acrylate terpolymers described in the Patent US-4,521,404, such as the product sold under the name GAFFIX VC 713 by GAF CORPORATION.

(2) Cellulose ether derivatives containing quaternary ammonium groups, described in French Pat. No. 1,492,597 and in particular the polymers marketed under the names "JR" (JR 400, JR 125, JR 30M) or "LR" (LR 400, LR 30M) by UNION CARBIDE CORPORATION. The polymers are also defined in the CTFA dictionary as quaternary ammonium compounds of hydroxyethylcellulose which have been reacted with an epoxide substituted with a trimethylammonium group.

(3) Cationic cellulose derivatives such as copolymers of cellulose or of cellulose derivatives grafted with a water-soluble quaternary ammonium monomer and described in greater detail in U.S. Pat. No. 4,131,576, such as hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products which correspond to this definition are more particularly the products sold under the names "CELQUAT L 200" and "CELQUAT H 100" by NATIONAL STARCH.

(4) Cationic polysaccharides described more particularly in U.S. Pat. Nos. 3,589,578 and 4,031,307 and more particularly the product marketed under the name "JAGUAR C. 13 S" sold by MEYHALL.

(5) Polymers which consist of piperazinyl units and divalent alkylene or hydroxyalkylene radicals, with straight or branched chains, optionally interrupted by oxygen, sulphur or nitrogen atoms or by aromatic or heterocyclic rings and products of oxidation and/or of quaternization of these polymers. Such polymers are described in French Pat. Nos. 2,162,025 and 2,280,361.

(6) Polyaminoamides such as (a) Water-soluble polyaminoamides prepared in particular by the polycondensation of an acid compound with a polyamine. These polyaminoamides may be cross-linked with an epihalohydrin, a diepoxide, a dianhydride, an unsaturated anhydride, a bis-unsaturated derivative, a bis(halohydrin), a bis(azetidinium), a bis(haloacyldiamine), a bis(alkyl halide) or with an oligomer resulting from the reaction of a bifunctional compound which is reactive towards a bis(halohydrin), a bis(azetidinium), a bis(haloacyldiamine), a bis(alkyl halide), an epihalohydrin, a diepoxide or a bis-unsaturated derivative; the crosslinking agent being employed in proportions ranging from 0.025 to 0.35 mole per amine group in the polyaminoamide.

These polyaminopolyamides may be alkylated or, if they contain one or more tertiary amine groups, be quaternized. Such polymers are described in particular in French Pat. Nos. 2,252,840 and 2,368,508.

(b) Polyaminoamide derivatives resulting from the condensation of polyalkylenepolyamines with polycarboxylic-acids followed by an alkylation with bifunctional agents. There may be mentioned, for example, adipic acid/dialkylaminohydroxyalkyldialkylenetriamine polymers in which the alkyl radical contains 1 to 4 carbon atoms and preferably denotes a methyl, ethyl or propyl radical. Such polymers are described in French Pat. No. 1,583,363.

Among these derivatives, adipic acid/dimethylaminohydroxypropyldiethylenetriamine polymers sold under the names "CARTARETINE F, F$_4$ or F$_8$" by SANDOZ may more particularly be mentioned.

(c) Polyaminoamides obtained by the reaction of a polyalkylenepolyamine containing two primary amine groups and at least one secondary amine group with a dicarboxylic acid chosen from amongst diglycollic acid and saturated aliphatic dicarboxylic acids containing 3 to 8 carbon atoms. The molar ratio between the polyalkylenepolyamine and the dicarboxylic acid is between 0.8:1 and 1.4:1; the polyaminoamide resulting therefrom is made to react with epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are in particular marketed under the name "HERCOSETT 57" by HERCULES INCORPORATED or under the name "PD 170" or "DELSETTE 101" by HERCULES in the case of the adipic acid/epoxypropyldiethylenetriamine copolymer.

(7) Cyclopolymers with a molecular weight from 20,000 to 3,000,000, such as homopolymers containing, as the main constituent of the chain, units corresponding to the formulae (VIII) or (VIII'):

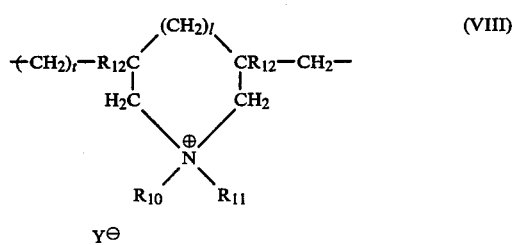

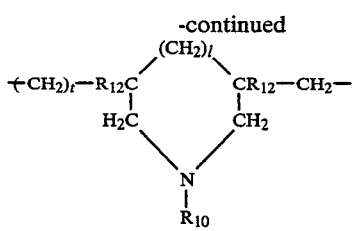

$l$ and $t$ are equal to 0 or 1, and the sum $l+t=1$, $R_{12}$ denotes hydrogen or methyl, $R_{10}$ and $R_{11}$ denote, independently from each other, an alkyl group containing 1 to 22 carbon atoms, a hydroxyalkyl group in which the alkyl group preferably has 1 to 5 carbon atoms, a lower amidoalkyl group, or alternatively, $R_{10}$ and $R_{11}$ may denote, together with the nitrogen atom to which they are attached, heterocyclic groups such as piperidinyl or morpholinyl, and copolymers comprising units of formulae (VIII) or (VIII') and units derived from acrylamide or from diacetone acrylamide, $Y^{\ominus}$ is an anion such as bromide, chloride, acetate, borate, citrate, tartrate, bisulphate, bisulphite, sulphate or phosphate.

Among the polymers defined above, there may be mentioned more particularly the dimethyldiallylammonium chloride homopolymer sold under the name MERQUAT 100, with a molecular weight less than 100,000 and the copolymer of dimethyldiallylammonium chloride and acrylamide, with a molecular weight greater than 500,000 and sold under the name MERQUAT 550 by MERCK.

These polymers are described more particularly in French Pat. No. 2,080,759 and the certificate of addition thereof No. 2,190,406.

(8) Poly(quaternary ammonium)polymers containing recurring units corresponding to the formula:

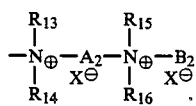

in which $R_{13}$ and $R_{14}$, and $R_{15}$ and $R_{16}$, which may be identical or different, represent aliphatic, alicyclic or arylaliphatic radicals containing 1 to 20 carbon atoms or lower hydroxyaliphatic radicals, or $R_{13}$ and $R_{14}$, and $R_{15}$ and $R_{16}$, together or separately form, with the nitrogen atoms to which they are attached, heterocycles optionally containing a second heteroatom other than nitrogen, or alternatively, $R_{13}$, $R_{14}$, $R_{15}$ and $R_{16}$ represent a straight-chain or branched $C_1$-$C_6$ alkyl radical substituted with a nitrile, ester, acyl, amide or:

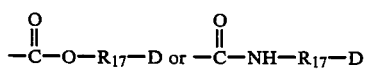

group, where $R_{17}$ is an alkylene group and D is a quaternary ammonium group.

$A_2$ and $B_2$ represent polymethylene groups containing 2 to 20 carbon atoms, which may be straight-chain or branched, saturated or unsaturated and may contain, attached thereto or inserted in the main chain, one or more aromatic rings or one or more oxygen or sulphur atoms or sulphoxide, sulphone, disulphide, amino, alkylamino, hydroxyl, quaternary ammonium, ureido, amide or ester groups and $X^{\ominus}$ denotes an anion derived from an inorganic or organic acid.

$A_2$ and $R_{13}$ and $R_{15}$ may form, with the two nitrogen atoms to which they are attached, a piperazine ring; additionally, if $A_2$ denotes a saturated or unsaturated straight-chain or branched alkylene or hydroxyalkylene radical, $B_2$ may also denote a group:

in which D denotes:

(a) a glycol residue of formula: —O—Z—O— where Z denotes a straight-chain or branched hydrocarbon radical or a group corresponding to the formulae:

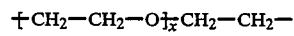

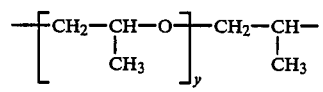

in which x and y denote an integer from 1 to 4, representing a defined and unique degree of polymerization, or any number from 1 to 4, representing an average degree of polymerization;

(b) a bis(secondary diamine)residue such as a piperazine derivative;

(c) a bis(primary diamine)residue of formula:

—NH—Y—NH— where Y denotes a straight-chain or branched hydrocarbon radical or the divalent radical:

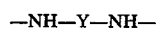

(d) a ureylene group of formula:

—NH—CO—NH—;

and $X^{\ominus}$ is an anion such as chloride or bromide.

These polymers have a molecular mass generally between 1,000 and 100,000.

Polymers of this type are described in particular in French Pat. Nos. 2,320,330, 2,270,846, 2,316,271, 2,336,434 and 2,413,907 and U.S. Pat. Nos. US-A-2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(9) Poly(quaternary ammonium)polymers consisting of units of formula:

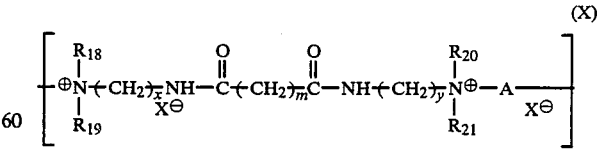

in which $R_{18}$, $R_{19}$, $R_{20}$ and $R_{21}$, which may be identical or different, represent a hydrogen atom or a methyl, ethyl, propyl, $\beta$-hydroxyethyl, $\beta$-hydroxypropyl or —$CH_2CH_2(OCH_2$—$CH_2)_pOH$ radical, where p is equal to 0 or to an integer between 1 to 6, on condition that $R_{18}$, $R_{19}$, $R_{20}$ and $R_{21}$ do not simultaneously represent a hydrogen atom, x and y, which may be identical or different, are integers between 1 and 6;

m is equal to 0 or to an integer between 1 and 34, $X^{\ominus}$ denotes a halide anion, and A denotes a radical of a dihalide and preferably represents:

$$-CH_2-CH_2-O-CH_2-CH_2-$$

Such compounds are described in greater detail in the Application EP-A-122,324.

(10) Homopolymers or copolymers derived from acrylic or methacrylic amides or esters and containing the units:

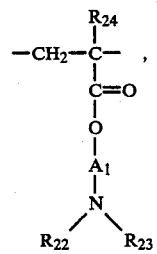  (XI)

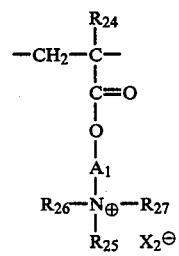  (XII)

or

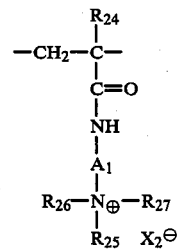  (XIII)

in which $R_{24}$ denotes H or $CH_3$, $A_1$ is a straight-chain or branched alkylene group containing 1 to 6 carbon atoms or a hydroxyalkylene group containing 2 to 4 carbonatoms, $R_{25}$, $R_{26}$ and $R_{27}$, which may be identical or different, represent an alkyl group containing 1 to 18 carbon atoms or a benzyl radical, $R_{22}$ and $R_{23}$ represent hydrogen or an alkyl group containing 1 to 6 carbon atoms, $X_2^{\ominus}$ denotes a methosulphate anion or a halide such as chloride or bromide.

The comonomer(s) which may be employed belong(s) to the family: acrylamide, methacrylamide, diacetone acrylamide, acrylamide and methacrylamide substituted at the nitrogen atom with lower alkyl radicals, esters of acrylic or methacrylic acids, vinylpyrrolidone and vinyl esters.

Among these compounds, there may be mentioned the copolymer of acrylamide and dimethylaminoethyl methacrylate quaternized with dimethylsulphate and sold under the name "HERCOFLOC" by HERCULES, the copolymer of acrylamide and methacryloyloxyethyltrimethylammonium chloride, described in the Patent Application EP-A-80,976, and sold under the name "BINA QAT P100" by CIBA GEIGY, or poly(methacrylamidopropyltrimethylammonium chloride) sold under the name "POLYMAPTAC" by TEXACO CHEMICALS.

(11) Quaternary polymers of vinylpyrrolidone and vinylimidazole, such as, for example, products marketed under the names LUVIQUAT FC 905, FC 550 and FC 370 by BASF.

(12) Polyamines such as Polyquart H sold by HENKEL, referred to by the name "POLYETHYLENE GLYCOL (15) TALLOW POLYAMINE" in the CTFA dictionary.

Other cationic polymers which may be employed according to the invention are polyalkyleneimines, in particular polyethyleneimines, polymers containing vinylpyridine or vinylpyridinium units, condensates of polyamines and epichlorohydrin, quaternary polyureylenes and chitin derivatives.

The particularly preferred cationic polymers according to the invention are:

cellulose ether derivatives containing quaternary ammonium groups such as those sold under the name "JR" such as, for example, JR 125, JR 400 and JR 30M, "LR" such as LR 400 and LR 30, by UNION CARBIDE CORPORATION.

copolymers of cellulose or of cellulose derivatives grafted with a water-soluble quaternary ammonium monomer such as products sold under the names: "CELQUAT L200" and CELQUAT H 100" by NATIONAL STARCH;

vinylpyrrolidone/dialkylaminoalkyl acrylate or methacrylate copolymers, which may be quaternized or otherwise, such as the products sold under the names "COPOLYMER 845", "GAFQUAT 734 or 755" by GAF;

quaternized polymers of the ionene type, described in the French Pat. No. 2,270,846 of the Applicatant Company and more particularly that comprising the units:

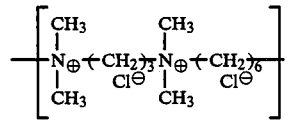  (XIV)

vinylcaprolactam/vinylpyrrolidone/dialkylaminoalkyl methacrylate or acrylate terpolymer such as the product sold under the name "GAFFIX VC 713";

quaternary ammonium polymers of the type described in U.S. Pat. No. 4,157,388 and more particularly the polymer comprising units of formula:

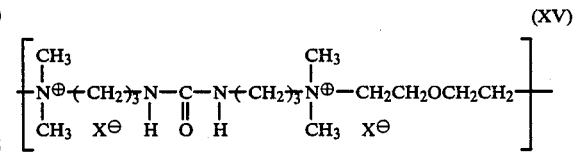  (XV)

in which $X^{\ominus}$ is a halide ion, sold under the name "MIRAPOL A 15" by MIRANOL;

poly(dimethylbutenylammonium chloride)-α,ω-bis(-triethanolammonium chloride)polymers sold under the name "ONAMER M" by ONYX INTERNATIONAL;

the polymer comprising units of formula:

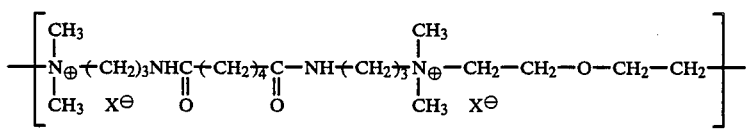

(XVI)

in which $X^\ominus$ is a halide, sold under the "MIRAPOL AD 1" by MIRANOL; and the polymer comprising units of formula:

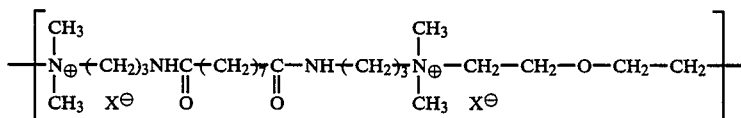 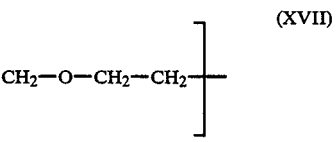

(XVII)

in which $X^\ominus$ is a halide, sold under the name "MIRAPOL AZ 1" by MIRANOL.

The alkyloxazoline polymer is present in the compositions according to the invention in concentrations preferably between 0.05 and 8% by weight relative to the total weight of the composition, and in particular between 0.1 and 5% by weight, and the cationic polymer is employed in concentrations preferably between 0.05 and 8% by weight relative to the total weight of the composition, and preferably between 0.1 and 5% by weight, and more particularly between 0.2 and 3% by weight relative to the total weight of the composition.

The compositions according to the invention may be in various forms such as liquid, cream, milk, gel or thickened lotion and may be packaged in the form of aerosol and may be applied, in this case, either in the form of an aerosol spray or in the form of an aerosol foam.

The cosmetically acceptable medium may consist of water or a mixture of water and a cosmetically acceptable solvent such as, more particularly, a solvent chosen from amongst monohydric alcohols containing 1 to 8 carbon atoms such as ethanol, isopropanol, benzyl alcohol, phenylethyl alcohol, polyhydric alcohols such as alkylene glycols such as ethylene glycol, propylene glycol, and glycol ethers such as, for example, ethylene glycol monomethyl ether, ethylene glycol monoethyl ether and diethylene glycol monoethyl ether, used alone or in the form of a mixture. These solvents are present in proportions less than or equal to 70% by weight relative to the weight of the total composition.

When the compositions are packaged in the form of aerosol, they are packaged in the presence of a propellant gas such as carbon dioxide, nitrogen, nitrous oxide or volatile hydrocarbons such as butane, isobutane or propane and preferably chlorinated or fluorinated hydrocarbons.

These compositions may contain any other ingredient which is commonly employed in cosmetics, such as perfumes, colouring agents which may have the role of colouring the composition itself or the hair, preservatives, sequestrants, thickeners, silicones, softeners, foam synergists, foam stabilizers, sunscreens, peptizing agents and electrolytes, as well as anionic, nonionic, cationic or amphoteric surfactants or the mixtures thereof.

Together with the polymers defined above, it is also possible to employ nonionic polymers known in themselves such as polyvinylpyrrolidone, the copolymer of vinylpyrrolidone and vinyl acetate or polyvinyl alcohol such as, for example, partially acetylated polyvinyl alcohol which may be employed as foaming agent when the compositions according to the invention are packaged in the form of aerosol.

The compositions according to the invention are employed for shaping or setting the hair. They may also be employed in the form of a cream or as treatment product to be applied after shampooing, dyeing, bleaching, permanent-waving or straightening of the hair.

The pH of these compositions is generally between 2 and 11, and preferably between 3 and 10, adjusted with alkalinizing or acidifying agents which are commonly employed in cosmetics.

The method for the cosmetic treatment of hair, which forms another subject of the invention, consists in applying the polymers defined above to moistened or dried hair, preferably by means of the compositions described above, for hair setting or hair shaping, the application not being followed by a rinsing The following examples are intended to illustrate the invention without, however, being limiting in nature.

EXAMPLE 1

A hair shaping lotion with the following composition is prepared:

| | |
|---|---|
| Poly(ethyloxazoline) of molecular weight 200,000, sold under the name POLYMER XAS 10874-03 by DOW CHEMICAL | 0.6 g |
| Vinylcaprolactam/vinylpyrrolidone/dimethylaminoethyl methacrylate cationic terpolymer, sold under the name GAFFIX VC 713 by GAF, at an AS concentration of 37% | 0.5 g AS |
| Ethyl alcohol q.s. | 30° |
| 2-Amino-2-methyl-1-propanol q.s. pH | 8.5 |
| Perfumes, colouring agent, preservative q.s. | |
| Water q.s. | 100 g |

This lotion, when applied to clean and wrung hair, gives it shape-retention and offers form-retention to the hair style.

EXAMPLE 2

A hair setting lotion with the following composition is prepared:

| | |
|---|---|
| Poly(ethyloxazoline) of molecular weight 50,000, sold under the name POLYMER XAS | |

| | |
|---|---|
| 10874-01 by DOW CHEMICAL | 2.0 g |
| Poly(vinylpyrrolidone/diethylamino-ethyl methacrylate) copolymer, sold under the name COPOLYMER 845 by GAF, at an AS concentration of 19% | 0.5 g AS |
| Silicone cationic polymer sold at an AS concentration of 35%, under the name UCAR SILICONE ALE 56 by UNION CARBIDE | 0.2 g AS |
| Lactic acid q.s. pH | 5 |
| Perfumes, colouring agent, preservative | |
| Water q.s. | 100 g |

When applied to clean and wrung hair, this lotion offers slight waviness and shape-retention to the hair style, helps in disentangling and gives softness to the hair.

EXAMPLE 3

A hair styling lotion with the following composition is prepared:

| | |
|---|---|
| Poly(ethyloxazoline) of molecular weight 50,000, sold under the name POLYMER XAS 10874-01 by DOW CHEMICAL | 0.5 g |
| Quaternary ammonium polymer sold under the neme MIRAPOL A 15 by MIRANOL at an AS concentration of 68% | 0.5 g AS |
| Lactic acid q.s. pH | 7 |
| Ethyl alcohol q.s. | 10° |
| Perfumes, colouring agent, preservative q.s. | |
| Water q.s. | 100 g |

When applied to clean and wrung hair, this lotion gives liveliness and softness to the hair.

EXAMPLE 4

A hair styling foam with the following composition is prepared:

| | |
|---|---|
| Poly(ethyloxazoline) of molecular weight 200,000, sold under the name POLYMER XAS 10874-03 by DOW CHEMICAL | 1.0 g |
| Copolymer of hydroxyethylcellulose grafted with diallyldimethylammonium chloride sold under the name CELQUAT L 200 by NATIONAL STARCH | 1.0 g |
| 2-Amino-2-methyl-1-propanol q.s. pH | 8 |
| Perfumes, preservative q.s. | |
| Water q.s. | 100 g |

This composition is packaged in the form of aerosol.

| | |
|---|---|
| Above composition: | 90 g |
| Propellant: Freons 114/12 (43-57) | 10 g |

This foam, when applied to clean and wrung hair, gives them slight waviness, liveliness and softness.

EXAMPLE 5

A hair styling foam with the following composition is prepared:

| | |
|---|---|
| Poly(ethyloxazoline) of molecular weight 500,000, sold under the name POLYMER XAS 10874-05 by DOW CHEMICAL | 0.5 g |
| Copolymer of hydroxyethylcellulose grafted with diallyldimethylammonium chloride sold under the name CELQUAT L 200 by NATIONAL STARCH | 1.0 g |
| Quaternized protein, sold at an AS concentration of 43.7%, under the name CROQUAT S by CRODA | 0.2 g AS |
| 2-Amino-2-methyl-1-propanol q.s. pH | 8.5 |
| Ethyl alcohol q.s. | 10° |
| Perfumes, preservative q.s. | |
| Water q.s. | 100 g |

This composition is packaged in the form of aerosol.

| | |
|---|---|
| Above composition: | 90 g |
| Propellant: Freons 114/12 (43-57) | 10 g |

The foam, when applied to clean and wrung hair, gives it softness and liveliness.

EXAMPLE 6

A hair setting lotion with the following composition is prepared:

| | |
|---|---|
| Poly(ethyloxazoline) of molecular weight 200,000, sold under the name POLYMER XAS 10874-03 by DOW CHEMICAL | 1.5 g |
| Copolymer of hydroxyethylcellulose grafted with diallyldimethylammonium chloride, sold under the name CELQUAT L 200 by NATIONAL STARCH | 1.5 g |
| Poly(vinylpyrrolidone/diethylamino-ethyl methacrylate) copolymer, sold at an AS concentration of 20%, under the name COPOLYMER 937 by GAF | 1.0 g AS |
| Isopropyl alcohol | 20.0 g |
| Perfume, colouring agent preservative q.s. | |
| Spontaneous pH = 5.5 | |
| Water q.s. | 100 g |

When applied to clean and wrung hair, this lotion gives it slight waviness and liveliness.

EXAMPLE 7

A hair shaping lotion with the following composition is prepared:

| | |
|---|---|
| Poly(ethyloxazoline) of molecular weight 50,000, sold under the name POLYMER XAS 10874-01 by DOW CHEMICAL | 3.0 g |
| Protein hydrolysate containing a polypeptide chain with a molecular weight of approximately 12,000 and quaternary ammonium groups carrying at least one $C_1$–$C_{18}$ alkyl group, sold under the name CROTEIN Q by CRODA | 0.3 g |
| Quaternized polyvinylpyrrolidone copolymer of molecular weight 100,000, sold by GAF under the name GAFQUAT 734, at an AS concentration of 50% | 3.0 g AS |
| Perfume, colouring agent, preservative q.s. | |
| Ethylene glycol monoethyl ether | (10% by weight) |
| Ethyl alcohol (50% by weight) | q.s. 100 g |
| Water (40% by weight) | |
| Lactic acid q.s. | pH = 5 |

15

This lotion, in a slightly thickened form, when applied to clean and wrung hair, gives slight waviness and shape-retention to the hair style.

EXAMPLE 8

A hair styling milk with the following composition is prepared:

| | |
|---|---|
| Poly(ethyloxazoline) of molecular weight 200,000, sold under the name POLYMER XAS 10874-03 by DOW CHEMICAL | 5.0 g |
| Adipic acid/dimethylaminohydroxypropyl-diethylenetriamine copolymer, sold at an AS concentration of 30% by SANDOZ under the name CARTARETINE F4 | 1.0 g AS |
| Cationic polymer described in and prepared according to French Patent 2,270,846, consisting of recurring units of formula: 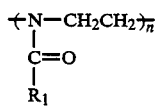 | 1.0 g |
| Silicone cationic polymer, sold by DOW CORNING under the name DOW CORNING Q2 7224 at an AS concentration of 35% | 0.1 g AS |
| Perfume, preservative q.s. | |
| Spontaneous pH = 8 | |
| Water q.s. | 100 g |

When applied to clean and wrung hair, this milk gives it slight waviness and facilitates disentangling.

EXAMPLE 9

A hair styling gel with the following composition is prepared:

| | |
|---|---|
| Poly(ethyloxazoline) of molecular weight 500,000, sold under the name POLYMER XAS 10874-05 by DOW CHEMICAL | 0.5 g |
| Copolymer of acrylamide and dimethylaminoethyl methacrylate, quaternized with dimethyl sulphate, sold under the name HERCOFLOC 1031 by HERCULES | 1.0 g |
| Perfume, colouring agent, preservative q.s. | |
| Spontaneous pH = 8 | |
| Water q.s. | 100 g |

This gel, when applied to hair, gives slight waviness to the hair style.

EXAMPLE 10

A hair styling milk with the following composition is prepared:

| | |
|---|---|
| Poly(ethyloxazoline) of molecular weight 500,000, sold under the name POLYMER XAS 10874-05 by DOW CHEMICAL | 0.3 g |
| Quaternized polymer of vinylpyrrolidone (5%) and vinylimidazole (95%), sold at an AS concentration of 40%, under the name LUVIQUAT FC 905 by BASF | 0.1 g AS |
| Polymer of hydroxyethylcellulose and epichlorohydrin quaternized with trimethylamine, sold under the name JR 400 by UNION CARBIDE | 0.5 g |
| Silicone cationic polymer, sold by DOW CORNING under the name EMULSION CATIONIQUE DC 929 (cationic emulsion DC 929) at an AS concentrate of 35% | 0.1 g AS |
| Opaqueing agent | 0.1 g |
| Perfume, preservative q.s. | |
| Ethyl alcohol | 10.0 g |
| Water q.s. | 100 g |

This milk, when applied to clean and wrung hair, gives shape-retention to the hair and facilitates disentangling.

EXAMPLE 11

A hair styling spray with the following composition is prepared:

| | |
|---|---|
| Poly(ethyloxazoline) of molecular weight 50,000, sold under the name POLYMER XAS 10874-01 by DOW CHEMICAL | 4.0 g |
| Poly(dimethylbutenylammonium chloride)-$\alpha,\omega$-bis(triethanolammonium chloride), sold at an AS concentration of 30%, under the name ONAMER M by ONYX INTERNATIONAL | 0.2 g AS |
| Isopropyl alcohol q.s. | 50° |
| Perfume, colouring agent q.s. | |
| Spontaneous pH = 6.5 | |
| Water q.s. | 100 g |

This lotion is packaged in a pump type dispenser. The spray obtained gives slight waviness and sheen to the hair.

We claim:

1. Cosmetic composition intended for hair treatment and care containing in a cosmetically acceptable medium, at least one alkyloxazoline polymer of formula $$+N-CH_2CH_2\frac{}{n}$$
$$|$$
$$C=O$$
$$|$$
$$R_1$$

in which $R_1$ is a $C_1$-$C_4$ alkyl radical, and n is such that the polymer has a molecular weight of at least 10,000, and at least one cationic polymer containing primary, secondary, tertiary and/or quaternary amine groups, which form part of the polymer chain or are linked thereto and which have a molecular weight between 500 and 5,000,000.

2. Composition according to claim 1, wherein the alkyloxazoline polymer is a ethyloxazoline homopolymer with a molecular weight between 10,000 and 1 million.

3. Composition according to claim 1, wherein the cationic polymer is a quaternized protein, a quaternized polysiloxane, a polymer of the class of quaternary polyammonium, polyaminoamides or polyamines or the mixture thereof.

4. Composition according to claim 3, wherein the quaternized protein consists of polypeptides which are modified chemically and which carry, at the end of the chain or grafted thereto, quaternary ammonium groups.

5. Composition according to claim 3, wherein the cationic polymer is selected from the groups comprising:
(1) vinylpyrrolidone/dialkylaminoalkyl acrylate or methacrylate copolymers, which may be quaternized or otherwise, or vinylcaprolactam/vinylpyrrolidone/dialkylaminoalkyl methacrylate or acrylate terpolymers;

(2) cellulose ether derivatives containing quaternary ammonium groups;

(3) copolymers of cellulose or of cellulose derivatives grafted with a water-soluble quaternary ammonium monomer;

(4) cationic polysaccharides;

(5) polymers which consists of piperazinyl units and divalent alkylene or hydroxyalkylene radicals, with straight- or branched-chain, optionally interrupted by oxygen, sulphur or nitrogen atoms or by aromatic or heterocyclic rings and products of oxidation and/or of quaternization of these polymers;

(6) polyaminoamides;

(7) cyclopolymers with a molecular weight from 20,000 to 3,000,000, containing, as the main constituent of the chain, units corresponding to the formulae (VIII) or (VIII'):

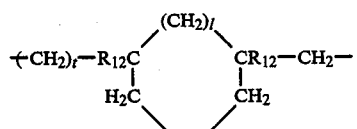
(VIII)

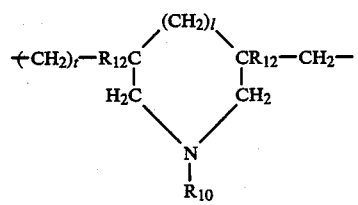
(VIII')

l and t are equal to 0 or 1, and the sum $l+t=1$, $R_{12}$ denotes hydrogen or methyl, $R_{10}$ and $R_{11}$ denote, independently from each other, an alkyl group containing 1 to 22 carbon atoms, a hydroxyalkyl group in which the alkyl group preferably has 1 to 5 carbon atoms, a lower amidoalkyl group, or alternatively, $R_{10}$ and $R_{11}$ may denote, together with the nitrogen atom to which they are attached, heterocyclic groups such as piperidinyl or morpholinyl, $Y^\ominus$ is an anion;

(8) quaternary polymers of vinylpyrrolidone and vinylimidazole;

(9) poly(quaternary ammonium)polymers containing recurring units corresponding to the formula:

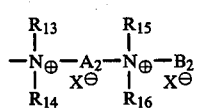

in which $R_{13}$ and $R_{14}$, and $R_{15}$ and $R_{16}$, which may be identical or different, represent aliphatic, alicyclic or arylaliphatic radicals containing 1 to 20 carbon atoms or lower hydroxyaliphatic radicals, or $R_{13}$ and $R_{14}$, and $R_{15}$ and $R_{16}$, together or separately form, with the nitrogen atoms to which they are attached, heterocycles optionally containing a second heteroatom other than nitrogen, or alternatively, $R_{13}$, $R_{14}$, $R_{15}$ and $R_{16}$ represents a straight-chain or branched $C_1$-$C_6$ alkyl radical substituted with a nitrile, ester, aryl, amide or:

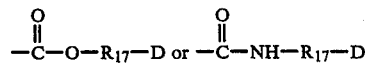

group, where $R_{17}$ is an alkylene group and D is a quaternary ammonium group;

$A_2$ and $B_2$ represent polymethylene groups containing 2 to 20 carbon atoms, which may be straight-chain or branched, saturated or unsaturated and may contain, attached thereto or inserted in the main chain, one or more aromatic rings or one or more oxygen or sulphur atoms or sulphoxide, sulphone, disulphide, amino, alkylamino, hydroxyl, quaternary ammonium, ureido, amide or ester groups and $X^\ominus$ denotes an anion derived from an inorganic or organic acid;

$A_2$ and $R_{13}$ and $R_{15}$ may form, with the two nitrogen atoms to which they are attached, a piperazine ring; additionally, if $A_2$ denotes a saturated or unsaturated straight-chain or branched alkylene or hydroxyalkylene radical, $B_2$ may also denote a group:

$-(CH_2)_n-CO-D-OC-(CH_2)_n-$ in which D denotes:

(a) a glycol residue of formula: $-O-Z-O-$ where Z denotes a straight-chain or branched hydrocarbon radical or a group corresponding to the formulae:

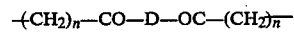

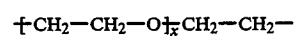

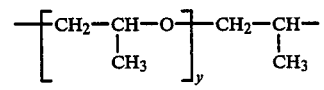

in which x and y denote an integer from 1 to 4, representing a defined and unique degree of polymerization, or any number from 1 to 4, representing an average degree of polymerization;

(b) a bis(secondary diamine)residue such as a piperazine derivative;

(c) a bis(primary diamine)residue of formula:

where Y denotes a straight-chain or branched hydrocarbon radical or a divalent radical:

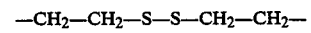

(d) a ureylene group of formula:

(10) poly(quaternary ammonium)polymers consisting of units of formula:

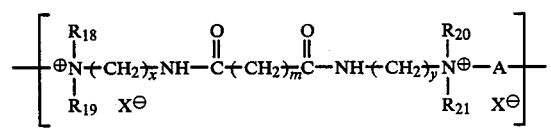

in which $R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$—CH$_2$)$_p$OH radical, where p is equal to 0 or to an integer between 1 and 6, on condition that R$_{18}$, R$_{19}$, R$_{20}$ and R$_{21}$ do not simultaneously represent a hydrogen atom, x and y, which may be identical or different, are integers between 1 and 6; m is equal to 0 or to an integer between 1 and 34; X$^\ominus$ denotes a halide anion, and A denotes a radical of a dihalide and preferably represents:

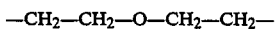

(11) homopolymers or copolymers derived from acrylic or methacrylic amides or esters and containing the units:

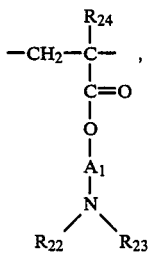

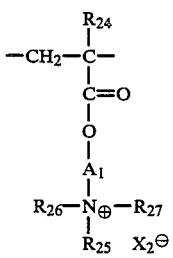

or $$-CH_2-\underset{\underset{\underset{\underset{\underset{R_{25}\ X_2^\ominus}{|}}{R_{26}-N_\oplus-R_{27}}}{|}}{\underset{|}{A_1}}}{\underset{|}{\underset{\|}{NH}}}{\overset{R_{24}}{\underset{|}{C}}}-$$

in which R$_{24}$ denotes H or CH$_3$; A$_1$ is a straight-chain or branched alkylene group containing 1 to 6 carbon atoms or a hydroxyalkylene group containing 2 to 4 carbon atoms; R$_{25}$, R$_{26}$ and R$_{27}$, which may be identical or different, represent an alkyl group containing 1 to 18 carbon atoms or a benzyl radical; R$_{22}$ and R$_{23}$ represent hydrogen or an alkyl group containing 1 to 6 carbon atoms; X$_2^\ominus$ denotes a methosulphate anion or a halide such as chloride or bromide;

(12) a polyamine referred to by the name "polyethylene glycol (15) tallow polyamine";

(13) polyalkyleneimines;

(14) polymers containing vinylpyridine or vinylpyridinium units;

(15) condensates of polyamines and epichlorohydrin;

(16) quaternary polyureylenes;

(17) chitin derivatives;

(18) poly(dimethylbutenylammonium chloride)-α, ω-bis(triethanolammonium chloride)polymers.

6. Composition according to claim 5, wherein the cationic polymer is:

a cellulose ether derivative containing quaternary ammonium groups;

a polymer of cellulose or of cellulose derivatives grafted with a water-soluble quaternary ammonium monomer;

a vinylpyrrolidone/dialkylaminoalkyl acrylate or methacrylate copolymer, quaternized;

a vinylcaprolactam/vinylpyrrolidone/dialkylaminoalkyl methacrylate or acrylate terpolymer;

a polymer comprising units of formula:

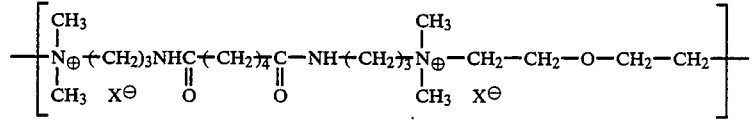

in which X$^\ominus$ is a halide;

a polymer comprising units of formula:

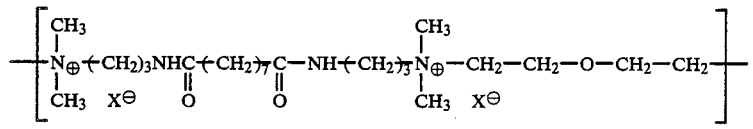

in which X$^\ominus$ is a halide;

a quaternized polymer comprising the units:

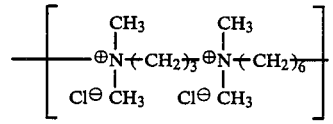

a quaternary ammonium polymer comprising units of formula:

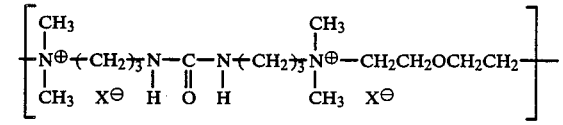

in which X$^\ominus$ is a halide ion; and
poly(dimethylbutenylammonium chloride)-α,ω-bis(triethanolammonium chloride) polymers.

7. Composition according to claim 1, wherein the polymers are present in the compositions in proportion of between 0.05 and 8% by weight relative to the total weight of the composition respectively.

8. Composition according to claim 1, which is in the form of a liquid, a cream, a milk, a gel, a thickened lotion or that it is packaged as aerosol in the form of a spray or a foam.

9. Composition according to claim 1, wherein the cosmetically acceptable medium contains water combined or otherwise with a cosmetically acceptable solvent chosen from amongst monoalcohols containing 1 to 8 carbon atoms, polyalcohols and glycol ethers, used alone or in the form of a mixture and the solvent(s) being present in proportions less than or equal to 70% by weight relative to the total weight of the composition.

10. Composition according to claim 1, containing in addition to the polymers, other ingredients which are commonly employed in cosmetics such as perfumes, colouring agents which may have the role of colouring the composition itself or the hair, preservatives, sequestrants, thickeners, silicones, softeners, foam synergists, foam stabilizers, electrolytes, sunscreens, peptizing agents and anionic, nonionic, cationic or amphoteric surfactants or the mixtures thereof.

11. Composition according to claim 1, also containing nonionic polymers other than the polymer derived from alkyloxazoline.

12. Process for the cosmetic treatment of hair which comprises applying thereto a composition containing in a cosmetically acceptable medium at least one alkyloxazoline polymer of formula:

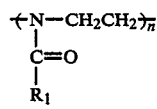

in which $R_1$ is a $C_1$–$C_4$ alkyl radical, and n is such that the polymer has a molecular weight of at least 10,000 and at least one cationic polymer containing primary, secondary, tertiary and/or quaternary amine groups, which form part of the polymer chain or are linked thereto and which have a molecular weight between 500 and 5,000,000.

13. Process according to claim 12, in which the application of the composition to the hair is not followed by a rinsing of the hair.

* * * * *